(12) United States Patent
Zhang et al.

(10) Patent No.: US 8,525,831 B2
(45) Date of Patent: Sep. 3, 2013

(54) METHOD AND APPARATUS FOR THREE-DIMENSIONAL VISUALIZATION AND ANALYSIS FOR AUTOMATIC NON-DESTRUCTIVE EXAMINATION OF A SOLID ROTOR USING ULTRASONIC PHASED ARRAY

(75) Inventors: Jingdan Zhang, Plainsboro, NJ (US); Moritz Michael Knorr, Bonn (DE); Shaohua Kevin Zhou, Plainsboro, NJ (US); Waheed A. Abbasi, Murrysville, PA (US); Michael F. Fair, Oakmont, PA (US); Larry C. Himes, Greensburg, PA (US); Michael J. Metala, Murrysville, PA (US); El Mahjoub Rasselkorde, Pittsburgh, PA (US)

(73) Assignees: Siemens Corporation, Iselin, NJ (US); Siemens Energy, Inc., Orlando, FL (US)

( * ) Notice: Subject to any disclaimer, the term of this patent is extended or adjusted under 35 U.S.C. 154(b) by 472 days.

(21) Appl. No.: 12/897,821

(22) Filed: Oct. 5, 2010

(65) Prior Publication Data
US 2011/0109627 A1 May 12, 2011

Related U.S. Application Data (60) Provisional application No. 61/248,545, filed on Oct. 5, 2009.

(51) Int. Cl.
*G06T 17/00* (2006.01)
(52) U.S. Cl.
USPC ............... 345/420; 345/419; 73/605; 73/623; 73/626; 382/117; 382/131; 382/276; 702/39

(58) Field of Classification Search
USPC ................. 345/419, 420; 73/605, 623, 626; 382/131, 117, 276; 702/39
See application file for complete search history.

(56) References Cited

U.S. PATENT DOCUMENTS

| | | | |
|---|---|---|---|
| 5,408,884 A | 4/1995 | Sabourin | |
| 5,601,083 A * | 2/1997 | Anderson | 600/443 |
| 5,880,961 A * | 3/1999 | Crump | 700/112 |
| 6,175,655 B1 * | 1/2001 | George et al. | 382/257 |
| 7,106,322 B2 * | 9/2006 | Deering | 345/419 |
| 7,302,851 B2 | 12/2007 | Czerw et al. | |
| 7,328,620 B2 | 2/2008 | Howard et al. | |
| 7,499,050 B2 * | 3/2009 | Wu et al. | 345/420 |
| 7,500,396 B2 | 3/2009 | Bentzel | |
| 7,606,445 B2 | 10/2009 | Howard | |
| 7,643,604 B2 * | 1/2010 | Jupiter et al. | 378/2 |
| 8,010,315 B2 * | 8/2011 | Wu et al. | 702/152 |
| 8,290,303 B2 * | 10/2012 | Washburn et al. | 382/294 |
| 8,326,011 B2 * | 12/2012 | Star-Lack et al. | 382/131 |

(Continued)

*Primary Examiner* — Kimbinh T Nguyen (57) ABSTRACT

A method and apparatus for three-dimensional visualization and analysis for automatic non-destructive examination of a solid Rotor using ultrasonic phased array is disclosed. Data is acquired by scanning a solid rotor with a phased array ultrasound transducer producing a plurality of two dimensional ultrasound scans. Each of a plurality of sample points of a plurality of two dimensional ultrasound scans are associated with a corresponding 3D image point of a regular grid. A kernel function for each of the plurality of sample points defining a size and shape of a kernel located at the corresponding image point is determined. A weight is assigned to each kernel which, in one embodiment, is based on the sample point value. A value for each image point of the regular 3D grid is determined based on kernels overlapping each image point. A three-dimensional volume representing the solid rotor is then visualized.

21 Claims, 10 Drawing Sheets

(56) References Cited

U.S. PATENT DOCUMENTS

| | | | |
|---|---|---|---|
| 2007/0217672 A1* | 9/2007 | Shannon et al. | 382/152 |
| 2009/0307628 A1* | 12/2009 | Metala et al. | 715/782 |
| 2012/0055252 A1* | 3/2012 | Boehm et al. | 73/620 |
| 2012/0113508 A1* | 5/2012 | Coleman et al. | 359/459 |

\* cited by examiner

METHOD AND APPARATUS FOR THREE-DIMENSIONAL VISUALIZATION AND ANALYSIS FOR AUTOMATIC NON-DESTRUCTIVE EXAMINATION OF A SOLID ROTOR USING ULTRASONIC PHASED ARRAY

This application claims the benefit of U.S. Provisional Application No. 61/248,545, filed Oct. 5, 2009, the disclosure of which is herein incorporated by reference.

BACKGROUND OF THE INVENTION

The present invention relates to non-destructive examination, and more particularly, to three-dimensional visualization and analysis for automatic non-destructive examination of solid rotors using ultrasound.

A rotor is a rotating component of a turbine or a generator and its reliability is a major concern to users such as electric utilities. To promote operation safety and prevent potential failures, Non-Destructive Examinations (NDEs) are performed regularly to inspect the integrity of rotors. One of the examinations is boresonic inspection in which ultrasound is used to detect defects and flaws in a rotor.

In a boresonic inspection, defects and flaws, if present in the rotor, are detected using ultrasound and reported as digital data. This digital information is evaluated to determine the size and extent of defects and flaws such as material discontinuities. Performing this determination is not a trivial task and involves engineering know-how as well as experience. However, even with this know-how and experience, many assumptions are typically made and safety factors accounted for in order to make a representative assessment of rotor integrity. As a result, many boresonic inspection systems have a high degree of conservatism in data analysis, causing inaccurate flaw size estimation. Accordingly, a more accurate and user friendly method for boresonic inspection of rotors is desirable.

BRIEF SUMMARY OF THE INVENTION

The present invention provides a method and apparatus for visualization and analysis for automatic non-destructive examination of a solid rotor using ultrasound.

In one embodiment, a method for generating a three dimensional visualization of a solid rotor based on a plurality of two dimensional ultrasound scans of the solid comprises associating each of a plurality of sample points of a plurality of two dimensional ultrasound scans with a corresponding 3D image point of a regular grid. A kernel function for each of the plurality of sample points defining a size and shape of a kernel located at the corresponding image point is determined. A weight is assigned to each kernel, in one embodiment, based on the sample point value. A value for each image point of the regular 3D grid is determined based on kernels overlapping each image point. In one embodiment, a three-dimensional volume representing the solid rotor is then visualized.

These and other advantages of the invention will be apparent to those of ordinary skill in the art by reference to the following detailed description and the accompanying drawings.

DETAILED DESCRIPTION

The present invention relates to a method and apparatus for visualization and analysis for automatic non-destructive examination of solid rotors using ultrasound. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. Embodiments of the present invention are described herein to give an understanding of the visualization and analysis method and apparatus.

A rotor is the rotating part of a mechanical device. Rotors generally comprise a shaft with a plurality of blades extending radially from the shaft. Typically, a working fluid, such as air or water, may move or be moved by the rotor blades. In one application, water is directed toward the rotor blades to turn the rotor. The shaft of a rotor in these types of applications is connected to an electricity producing device such as a generator. Rotor shafts may be solid or hollow. In present disclosure, the term solid rotor refers to a solid rotor shaft.

Figure 1:
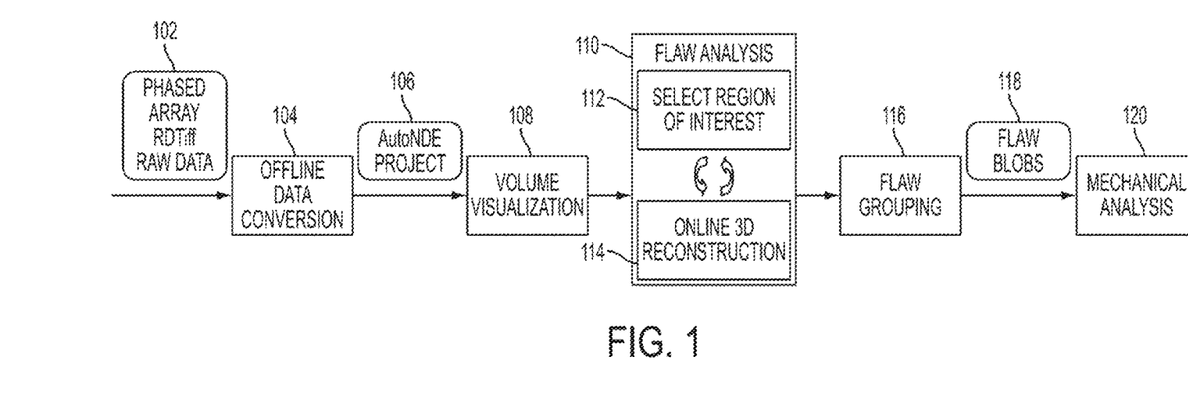
FIG. 1 illustrates an Automatic Non-Destructive Examination—Solid Rotor (AutoNDE-SR) system according to one embodiment.

FIG. 1 depicts one embodiment of Automatic Non-Destructive Examination-Solid Rotor (AutoNDE-SR) system which comprises four modules: offline data conversion module 104, visualization module 108, flaw analysis module 110, and flaw grouping module 116. Captured data representing information related to a solid rotor that has been scanned using an ultrasonic capturing device, in one embodiment, is stored in RDTiff files 102. Based on this raw data, offline conversion module 104 reconstructs volumes which convey the overall information represented by the data. RDTiff files 102, in one embodiment, also contain additional information pertaining to the data acquisition set up which is used by offline conversion module 104 to assure the correct configuration. After conversion, the data may be stored as an AUTONDE-SR project 106 which contains the converted volume and all necessary additional information such as the position of a solid rotor with respect to scanning equipment and the position of ultrasonic devices used to scan the solid rotor. Knowing the position of ultrasonic capturing devices with respect to the solid rotor during data acquisition allows the relationship between raw data and specific portions of the solid rotor to be determined. AutoNDE-SR project 106 is then loaded into visualization module 108 from which it can be visualized (i.e. displayed to a user), for example, on a display. Flaw analysis module 110 provides a series of tools that can be used to annotate flaws, remove noise, and generate high resolution volumes (online 3D reconstruction 114) in user identified (select region of interest 112) regions of interest (ROI). Flaw grouping module 116 groups flaws and estimates flaw sizes. Data regarding flaw groups are then output as flaw blobs 118 to mechanical analysis module 120 which applies fracture mechanics methodology to deterministically calculate the remaining life in cycles of the solid rotor.

A 3D volume conversion process, such as the conversion process performed by conversion module 104 of FIG. 1, comprises analyzing the captured data format, determining the acquisition set up parameters, and reconstructing the volume by resampling the data and performing 3D interpolation.

Ultrasound data representing a solid rotor is captured by scanning a solid rotor. Scanning a solid rotor differs from scanning a rotor bore in that a solid rotor has no hollow center section to facilitate insertion of a scanning tool such as an unitrasonic capturing device. The scanning operation for a solid rotor is further complicated by turbine blades attached about the circumference of the solid rotor. The characteristics of a phased array allow it to be utilized to scan a solid rotor without removal of attached turbine blades. Phased array ultrasound provides a representation of a solid rotor by capturing a reflection signal as a two dimensional (2D) B-Scan. A phased array transducer (also referred to as a capturing device) has an array of crystal elements wherein each element can be driven independent from the other elements. Using a certain delay pattern while driving the array, different focal laws can be realized. Compared to a one-dimensional A-Scan transducer, a flaw is hit by many more ultrasound beams from different directions when using a phased array transducer. This provides more information pertaining to a flaw and enables a lower degree of conservatism in flaw analysis and more accurate flaw size estimation.

Figure 2A:
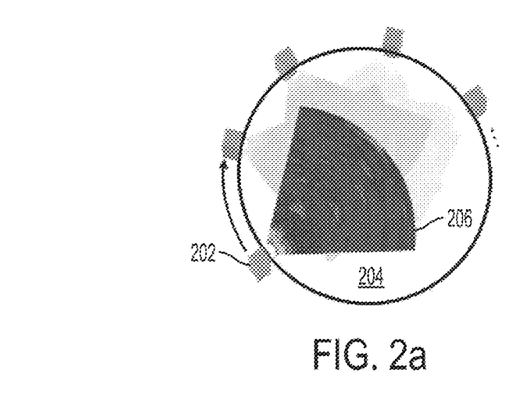
FIG. 2A illustrates a phased array transducer scanning a solid rotor.
Figure 2B:
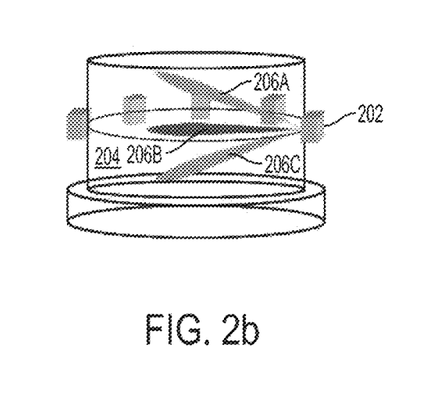
FIG. 2B illustrates a phased array transducer scanning a solid rotor at various angles of incidence.

A phased array transducer is capable of transmitting and receiving sound waves from almost any angle thereby allowing the capture of data pertaining to sections of a rotor beneath turbine blades. FIG. 2A illustrates capturing device 202, which, in one embodiment, is a phased array transducer. Capturing device 202 acquires two-dimensional (2D) B-scans 206 at different angles of incidence while rotating around the axis of solid rotor 204. FIG. 2B illustrates capturing device 202 scanning solid rotor 204 using different angles of incidence to capture data in different areas of solid rotor 204. As shown in FIG. 2B, scanner 206B scans the area of solid rotor 204 directly adjacent to capturing device 202. Different angles of incidence used for scans 206A and 206C allow areas of solid rotor 204 to be examined even though these area may not be accessible from the adjacent surface of the solid rotor because of turbine blades (not shown) located on the periphery of solid rotor 204 adjacent to the areas covered by scans 206A and 206C.

Figure 2C:
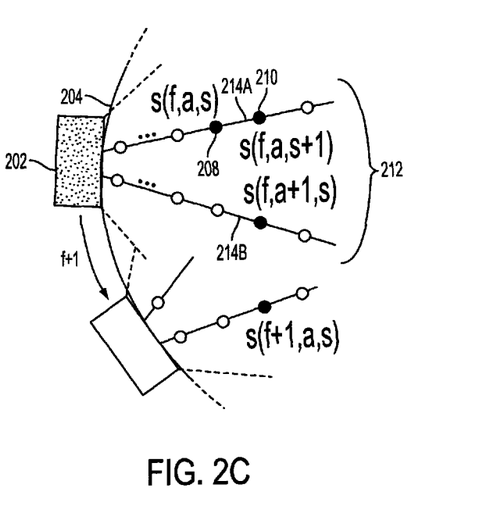
FIG. 2C illustrates a solid rotor scan pattern.

FIG. 2C illustrates a solid rotor scan pattern. Capturing device 202 is shown in two positions along the circumference of solid rotor 204. Each sampling point $P_s$ (208, 210 of FIG. 2C) is determined by three parameters, the fan number f, the A-Scan number a, and a sampling point number s. The amplitude value of the sample point is given by s(f, a, s) where $P_s=(f, a, s)^T$. Each fan 212 consists of several A-scans 214A, 214B with different orientations, that have a constant angle interval. This information can be used to determined the region of influence of each sampling point s(f, a, s). The Cartesian grid coordinates of the reconstructed volume are named i, j and k where $P_g=(i, j, k)^T$.

The number of capture positions around the axis and the number of B-scans at different angles of incidence at each capture position may vary. Further, different capturing devices and angles of incidence may be used in different axial positions. To account for these differences, acquisition set-up data and the captured data of each axial position are stored in an individual RDTiff file.

It should be noted that each 2D B-Scan, at each angle of incidence can be seen as a composition of individual one-dimensional (1D) A-Scans. As a consequence, the sampling grid may be highly irregular in that different areas of solid rotor 204 may be scanned with different sampling densities. This irregularity makes high demands on the reconstruction algorithm. In order to visualize the volume represented by the plurality of 2D B-Scans, a reconstruction algorithm need to resample the data to a regular 3D grid.

A backward mapping algorithm maps an image to a data space by searching the nearest sample positions in the data space. The data acquired during data acquisition results in a highly irregular sampling grid which results in the backward mapping algorithm being very time consuming. In a worst case scenario the position of every individual 1D A-Scan position has to do determined to check whether it affects an image sampling point. Further, the given geometry can lead to ambiguities in the computation.

A forward mapping algorithm maps data to an image space by identifying the image space sample positions which are affected by a data space sampling position.

In one embodiment, a forward mapping algorithm is used to map sample point data to an image space in which an assumption is made that every sample point in the data space represents a signal of a certain region. When the sample point is mapped to the image space, a particular sample point can affect multiple image space points but the influence of the particular sample point decreases over distance.

Figure 3:
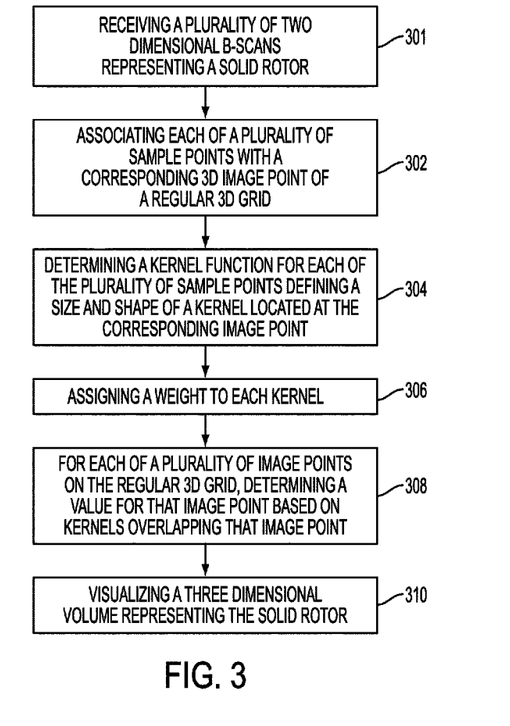
FIG. 3 illustrates a method for automatic non-destructive examination of a solid rotor according to one embodiment.

FIG. 3 illustrates a method for generating a three dimensional visualization of a solid rotor based on a plurality of two-dimensional B-Scans of the solid rotor according to one embodiment. At step 301, a plurality of B-Scans are received by offline data conversion module 104, in one embodiment, from a phased array transducer scanning a solid rotor (i.e. as the solid rotor is being scanned). In another embodiment, a solid rotor may be scanned and an acquired plurality of B-Scans are stored on a separate data storage device (not shown) before being transmitted, in total, to offline data conversion module 104. Each B-Scan is comprised of a plurality of sample points with each sample point representing a particular portion of the scanned solid rotor.

At step 302, each of the plurality of sample points of the plurality of two dimensional ultrasound scans are associated with a corresponding 3D image point of a regular 3D grid (e.g. a 3D space comprised of multiple stacked layers of cubes (or cuboids) arranged in columns and rows). The regular 3D grid is the framework which is used to construct a volume representing the scanned solid rotor. A particular sample point can be associated with a particular image point using data acquisition set up information contained in the RDTiff file with a related B-Scan. The data acquisition set up information describes how the plurality of scans are related to the solid rotor allowing the entire solid rotor to be accurately reconstructed in three dimensions on the regular 3D grid. It should be noted that each sample point can be associated with a particular corresponding image point on the 3D regular grid. Thus, every sample point has a corresponding image point. However, because of sampling constraints, not every image point of the 3D grid may have a corresponding sample point. Values for image points not having a corresponding sample point may be generated by interpolation using kernel functions.

Since different B-Scans can include data pertaining the same section of a solid rotor, multiple sampling points may represent the same portions of a solid rotor from different angles. Because these sample points describe reflection properties at different angles, no information should be omitted. However, since high amplitudes indicate a flaw or crack boundary in the solid rotor, high amplitudes are of more interest than low amplitudes. From these two considerations two different approaches are used. Specifically, a maximum and an average algorithm.

The maximum algorithm suppresses low amplitudes and conserves only the maximum within a certain region. The maximum algorithm is expressed as the equation:

$$v_{max}(i, j, k) = \underset{s(f,a,s)}{\mathrm{argmax}}(s(f, a, s) \cdot w_{max,f,a,s}(i, j, k))$$

In the average algorithm, the influence of a sampling point does not depend on its value but only on its distance to a grid point. The average algorithm is expressed as the equation:

$$v_{avg}(i, j, k) = \frac{\sum_{f,a,s} s(f, a, s) \cdot w_{avg,f,a,s}(i, j, k)}{\sum_{f,a,s} w_{avg,f,a,s}(i, j, k)}$$

The weighting functions $w_{max, f, a, s}(i, j, k)$ and $w_{avg, f, a, s}(i, j, k)$ determine the energy spread of each sampling points, or in other words, the influence of each sampling point in the reconstructed volume, for both equations, respectively.

Returning to FIG. 3, at step 304, a kernel function for each of the plurality of sample points defining the size and shape of a kernel located at the corresponding image point is determined. A kernel is a footprint of a sample point in the form of a 3D volume and is used to determine the impact of a particular sample point on the corresponding image point and surrounding image points. The shape of a kernel depends on the sampling rate in different dimensions and may be formed isotropic or elliptical. In order to optimize the speed of the process, a triangle kernel function may be used. The triangle kernel function is determined by approximating the non-triangular shape of signals represented by the B-Scan data with an appropriately sized and shaped triangle in order to simplify further computations.

Figure 11:
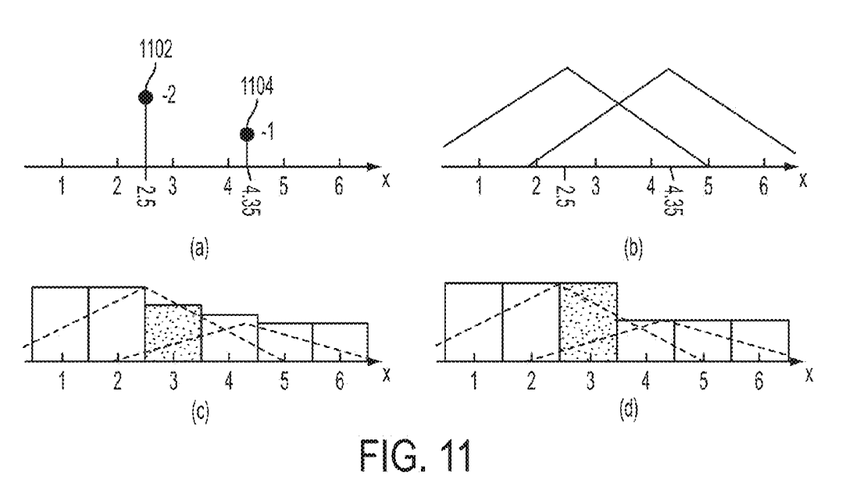
FIG. 11 illustrates reconstruction of a 1D signal using different algorithms.

FIG. 11 images a-d depict the different behaviors of the maximum and average algorithms based on a 1D signal. FIG. 11 image a depicts two sampling points 1102, 1104 located at 2.5 and 4.35 with amplitudes 2 and 1 respectively. FIG. 11 image b depicts non weighted triangle kernels located at the sampling point positions. FIG. 2 images c and d depicts the results of the average and maximum algorithms respectively. The result value at x=3 is either 1.635 or 2.0 depending on the algorithm used.

The Gaussian function is expressed as the equation:

$$\Sigma_{f,a,s} = \begin{bmatrix} \sigma^2_{i,f,a,s} & 0 & 0 \\ 0 & \sigma^2_{j,f,a,s} & 0 \\ 0 & 0 & \sigma^2_{k,f,a,s} \end{bmatrix}$$

where $\Sigma_{f, a, s}$ determines the shape and ratio of the Gaussian function.

The speed of the process may also be optimized using what is referred to as a fast algorithm. In the fast algorithm, each sample point is associated with a voxel. If two sample points are associated with a single voxel, the sample points are fused using either the average or maximum algorithm. A kernel with a fixed size and shape is then applied to every voxel to spread each sampling point's affect within each voxel. Although this fast algorithm is less accurate because a kernel's size and shape are fixed and not determined based on sampling, the fast algorithm allows quick reconstruction allowing a user to identify regions of interest which can then be reconstructed using a more accurate technique.

Returning to FIG. 3, at step 306, a weight is assigned to each kernel based on the value of the sample point associated with the kernel. In one embodiment, the kernel is weighted with the value of its associated sample point. A kernel's weight affects the influence of each sampling point in the reconstructed volume. The weighting function $w_{f, a, s}(i, j, k)$ describes the region and strength of the influence of each sampling point and is expressed by the equation:

$$w_{f,a,s}(p_g) = \frac{1}{(2\pi)^{\frac{3}{2}} \cdot |\Sigma|^{\frac{1}{2}}} e^{-\frac{1}{2}\left(\left(R_{f,a}^{-1}\cdot\left(p_g - \mu_{f,a,s}\right)\right)^t \cdot \Sigma_i^{-1} \cdot \left(R_{f,a}^{-1}\cdot\left(p_g - \mu_{f,a,s}\right)\right)\right)}$$

At step 308, a value for each of a plurality of image points on the regular 3D grid is determined based on kernels overlapping each image point. Each kernel may cover multiple image points and many image points may be covered by multiple overlapping kernels. The value for each image point in the 3D grid is determined based on the value assigned to that image point by the kernels overlapping that image point. The sampling along a radial axis is typically dense resulting in multiple overlapping kernels along the radial axis. The circumferential spacing between sampling points is typically larger than the radial spacing of the sampling points and in some cases may be ten to one hundred times larger. Kernel size and shape may be adapted to compensate for radial and circumferential sampling density.

The steps are repeated as necessary for each image point to visualize a desired volume or section of a volume representing the solid rotor. This process is referred to as elliptical weighted average volume splatting (EWA volume splatting). It should be noted that the process described above uses a triangle kernel function to optimize the speed at which the process can be performed. However, the present invention is not limited thereto, and other types of functions, such as a Gaussian kernel function could also be used.

Modifying image points based on overlapping kernels can cause averaging which can lead to the erosion of single signal peaks (e.g., cracks which can only be seen from one angle) which may cause a flaw not to be visualized in the 3D volume. In order to ensure that single signal peaks appear in the final volume visualization regardless of the surrounding data, in one embodiment, a conservative maximum approach can be used to determine the value of each image point based on overlapping kernels. The conservative maximum approach suppresses low amplitude signals and conserves only the maximum within a certain region. In one embodiment, an average approach is used in which the influence of a particular image point does not depend on the value of the image point but only on the image point's distance to a particular grid point.

Figure 12:
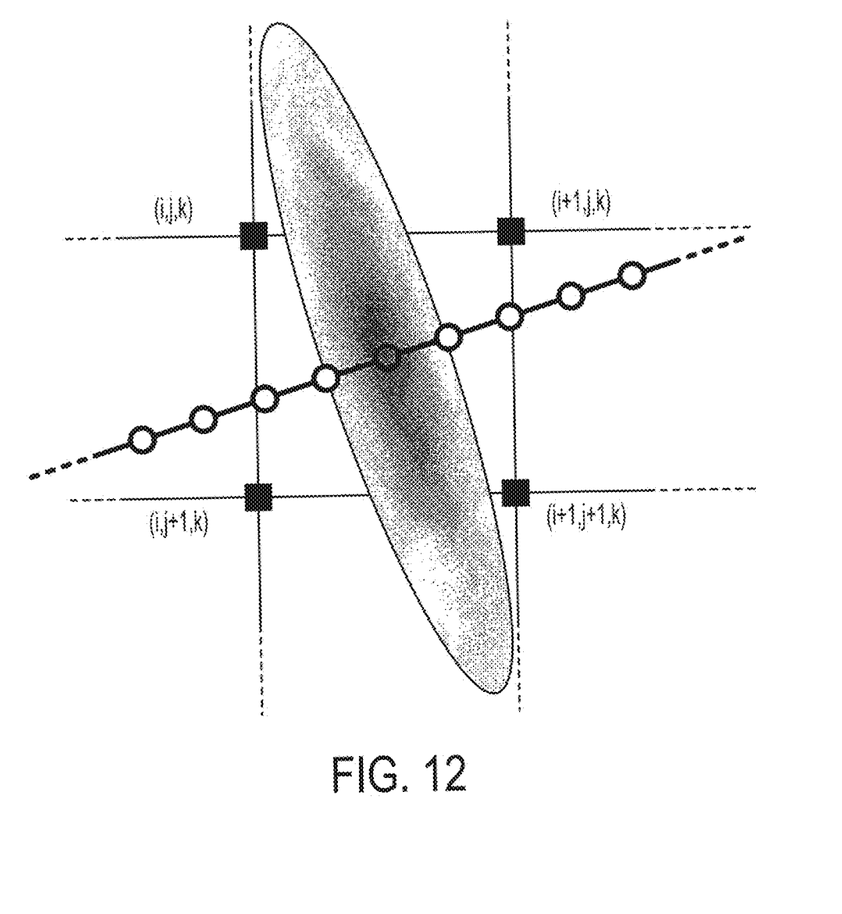
FIG. 12 illustrates the problem aliasing due to dense sampling along an A-scan line.

The kernel extent is important to prevent holes, aliasing, and over-blur. Usually, the sampling along the A-scan axis is very dense, whereas the distance between two neighboring A-scans might be ten to hundreds of times larger. In one embodiment, the kernel size is chosen to be twice the length to the neighboring A-scan or sampling point in each dimension. FIG. 12 illustrates the problem of aliasing. The dense sampling along the A-scan causes some kernels to "fall through the grid." This is disadvantageous because some sampling points will be represented in the result and others will not. In volume rendering this problem can be solved by extending the kernel size or adding the contribution to the nearest neighboring voxel. In signal processing, a signal will be low pass filtered to prevent aliasing during the resampling process. Therefore the kernel is enlarged in those dimensions where it might fall through the grid.

Figure 4:
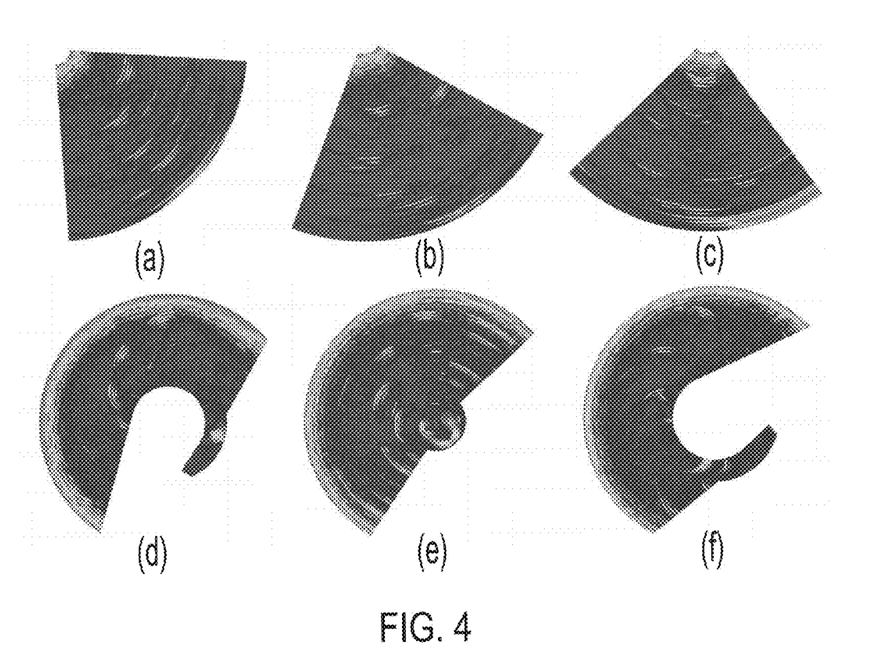
FIG. 4 illustrates different scans of a solid rotor received from a phased array transducer.
Figure 5:
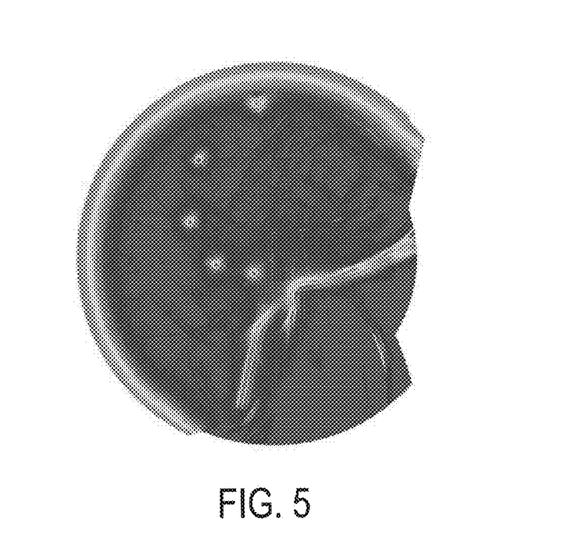
FIG. 5 illustrates several of the scans of FIG. 4 fused into one image.

FIG. 4 images a-c depict three B-Scans each taken at a different capture position and partially overlapping portions of the solid rotor being examined. As can be seen in FIG. 4 images a-c, it is difficult to find corresponding points representing a flaw or material discontinuity across the images. FIG. 4 images d-f depict the volume reconstruction result when using only one angle of incidence (also referred to as one focal law) when rotating about the axis of a solid rotor. In order to provide a clearer visualization of the flaws or material discontinuities, data captured from different positions are fused together. FIG. 5 depicts the volume reconstruction result when all data captured from different positions are fused together.

Figure 6:
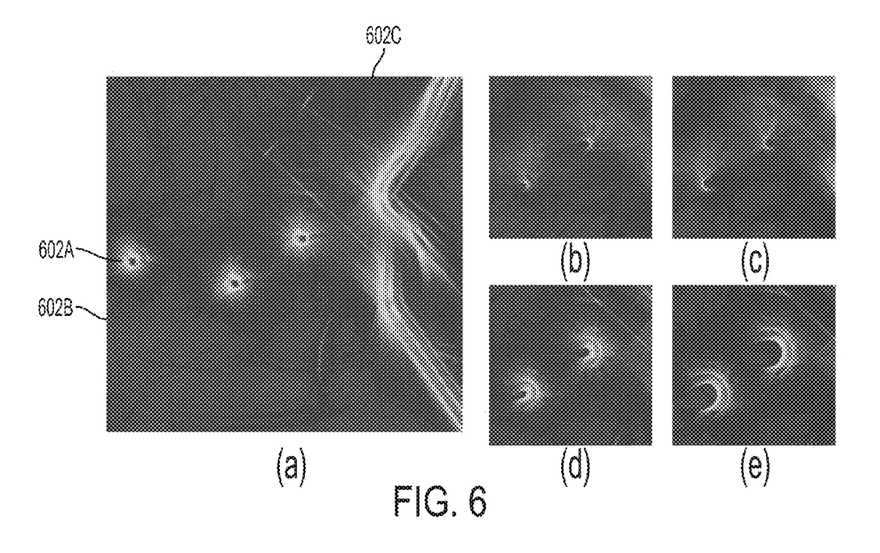
FIG. 6 illustrates the affect of various parameter adjustments on a reconstructed volume.

Accurate determination of flaw size, shape, and orientation requires high accuracy in the determination of data acquisition settings such as the speed of sound in the object being scanned and the wedge angle of the phased array transducer signals. FIG. 6 images a-e depict different reconstruction results before and after adjusting values pertaining to data acquisition settings. FIG. 6 image a depicts a solid rotor with three side drill holes 602a-602c. In the upper right corner, two flat bottom holes and their tips can be seen. The images depicted in FIG. 6 images a-e were generated from 2D B-Scans using the EWA splatting algorithm using a triangle kernel function. FIG. 6 image b depicts the initial reconstruction result. In FIG. 6 image b the speed of sound in the material of the solid rotor is not accurate and the wedge angle was not set correctly. As a result, the two bottom drill holes are open and the signal spreads widely as shown in FIG. 6 image b. Setting the wedge offset to −4.0 degrees results in the image shown in FIG. 6 image d in which the holes are still open but the signal is more concentrated around each hole. The detected or predicted speed of sound in the solid rotor can be used to adjust the reconstruction of images. Since the holes in the solid rotor are small, minute changes in the speed of sound parameter used to reconstruct the image can cause variances in the size estimation which may be larger than the flaw size. FIG. 6 image a depicts the reconstruction of an image using an offset of −2.25%. Changing the offset to +2.25% results in the image shown in FIG. 6 image e in which a different diameter estimation of hole size can be made. FIG. 6 image c shows the reconstruction after adjustment of the speed of sound parameter. FIG. 6 images d and e depict angular adjusted reconstructed images. FIG. 6 image b depicts a reconstructed image in which the speed of sound parameter is adjusted without wedge angle correction. Wedge angle refers to the angle between the 0 degree focal law of the phased array transducer and the normal of a rotor surface. If the phased array transducer does not couple the geometry of the surface of the solid rotor, the wedge angle is not zero which can lead to a low volume reconstruction quality. A phased array transducer which couples well with the geometry of the surface of the solid rotor requires little or no wedge angle correction. A phased array transducer which does not couple well with the surface of the solid rotor requires an corresponding amount of wedge.

As depicted in FIG. 6 images a-e, parameter adjustment affects size estimation of small flaws. Although the flaw position varies with parameter adjustment, because of the high number of measurements, the flaw position is easier to determine. For these reasons, Distance Gain Size (DGS) and other amplitude based methods can be used for analysis of small flaws. For larger flaws, echo dynamic pattern or time-of-flight flaw sizing methods can be used.

Figure 7:
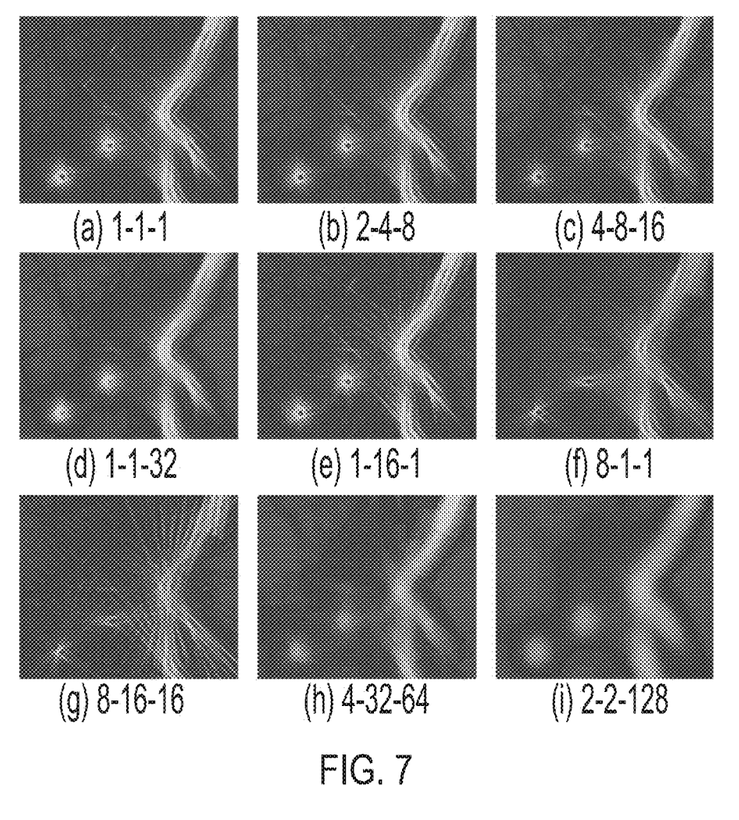
FIG. 7 illustrates the effect of file size compression on volume reproduction.

Due to the large number of RDTiff files involved in one project according to one embodiment, the file size of each RDTiff file affects the speed of reconstruction. The size of the RDTiff files is determined in part by the sampling rate. FIG. 7 images a-i depict examples of sample rate reduction. The data contained in an RDTiff file can be scaled in three dimensions: through the number of sampling points in each scan; through the number of capture positions around the solid rotor; and through the number of angles of incidence at each capture position.

FIG. 7 image a depicts a reconstruction result in the highest quality available. The file size of the RDTiff file which was used to generate the image shown in FIG. 7 image a is 150 MB. Using RDTiff files of this size can result in a large amount of data. In addition, these large files need to be opened and read during offline and online conversion which slows reconstruction speed considerably. To increase reconstruction speed, the file sizes can be reduced. However, the reduction of file size needs to be balanced with maintaining a reconstruction result that can be used to analyze flaws. FIG. 7 images d-f depict the results of data reduction in each dimension as indicated under each image. The reduction of sample positions along the A-Scans results in blurring whereas a reduction of focal laws and capture positions will result in a good spread. FIG. 7 image b depicts a reconstruction to $1/64^{th}$ of the original amount of data in which the reconstruction may still be used to analyze flaws. FIG. 7c depicts an image based data that has been reduced too much resulting in the depiction of flaws which are blurred and spread apart. FIG. 7 images g-i depict images in which the data reduction is more drastic resulting in reconstructions with have little value with respect to flaw analysis. A combination of scaling in different dimensions produces the best results and can reduce the amount of data from 150 MB to 3 MB for each RDTiff file.

Figure 8:
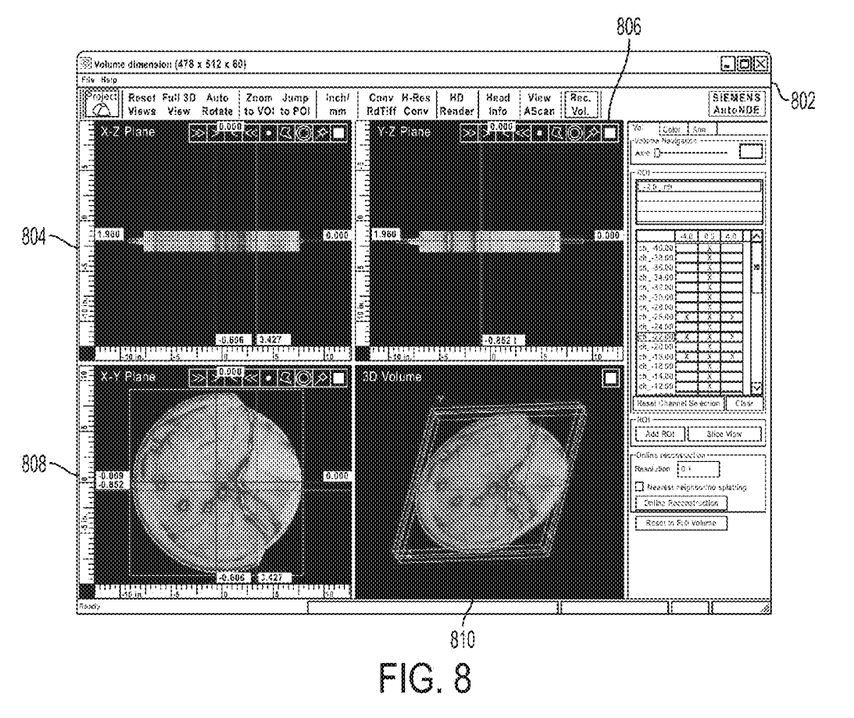
FIG. 8 illustrates a graphical user interface according to one embodiment.

Returning to FIG. 3, at step 310 the reconstructed 3D volume representing the solid rotor can be visually displayed. For example, the 3D volume can be displayed on a graphical user interface (GUI) on a display of a computer. FIG. 8 depicts an exemplary graphical user interface 802 according to one embodiment in which 2D and 3D images can be viewed and manipulated by a user. The reconstructed volume is shown visualized in four connected views 804, 806, 808, and 810. Views 804, 806, and 808 display a 2D cut through a volume and 810 shows a 3D view of the volume.

Figure 9:
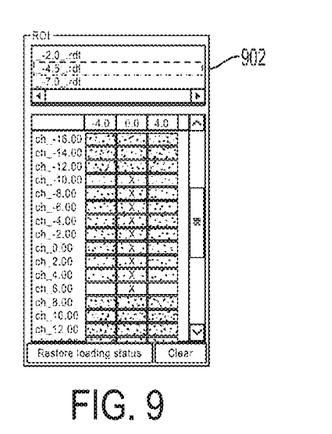
FIG. 9 illustrates a display showing the intensity of sample points and parameter settings.

In one embodiment, a portion of the total volume of a solid rotor can be displayed at a lower resolution to compensate for limitations of hardware used to support GUI 802 and increase the speed of reconstruction. Particular regions of a volume can be selected by a user to be reproduced in a higher resolution to provide a more detailed view of the particular region which aids in flaw analysis. After defining a region of interest, a table is generated displaying which channels and RDTiff files have been used for the reconstruction of the particular regions. FIG. 9 depicts table 902 according to one embodiment in which the maximum intensity of each channel in the region is indicated by different shading. In one embodiment, the maximum intensity of each channel in the region is indicated by different colors. Table 902 allows a user to quickly visualize the data structure and to identify noisy channels. The graphical user interface may also be used to assist a user with identifying flaws in a solid rotor.

Figure 10:
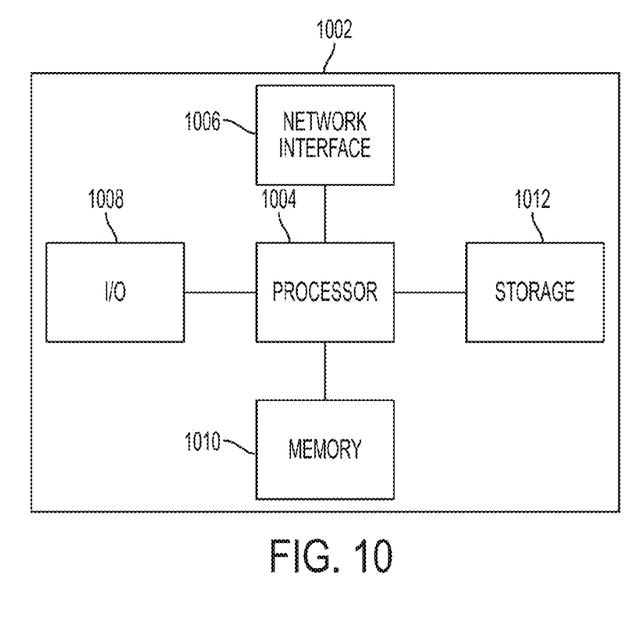
FIG. 10 is a high level block diagram of a computer capable of implementing the present invention.

The above-described methods for three-dimensional visualization and analysis for AutoNDE-SR using ultrasonic phased array may be implemented on a computer using well-known computer processors, memory units, storage devices, computer software, and other components. A high level block diagram of such a computer is illustrated in FIG. 10. Computer 1002 contains a processor 1004 which controls the overall operation of the computer 1002 by executing computer program instructions which define such operation. The computer program instructions may be stored in a storage device 1012, or other computer readable medium, (e.g., magnetic disk) and loaded into memory 1010 when execution of the computer program instructions is desired. Thus, all method steps described above, including the method steps illustrated in FIG. 3, may be defined by the computer program instructions stored in the memory 1010 and/or storage 1012 and controlled by the processor 1004 executing the computer program instructions. The computer 1002 also includes one or more network interfaces 1006 for communicating with other devices via a network. The computer 1002 also includes other input/output devices 1008 that enable user interaction with the computer 1002 (e.g., display, keyboard, mouse, speakers, buttons, etc.) One skilled in the art will recognize that an implementation of an actual computer could contain other components as well, and that FIG. 10 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method comprising:
generating a three dimensional visualization of a solid rotor based on a plurality of two dimensional ultrasound scans of the solid rotor by:
associating, at a processor, each of a plurality of sample points of the plurality of two dimensional ultrasound scans with a corresponding 3D image point of a blank regular 3D grid;
determining a kernel function for each of the plurality of sample points defining a size and shape of a kernel located at the corresponding image point;
assigning a weight to each kernel; and
for each of a plurality of image points on the regular 3D grid, determining a value for that image point based on kernels overlapping that image point.

2. The method of claim 1 further comprising:
receiving the plurality of two dimensional ultrasound scans.

3. The method of claim 2 wherein the plurality of two dimensional scans are acquired using a phased array transducer.

4. The method of claim 1 wherein the kernel associated with the sample point is one of isotropic and elliptical form.

5. The method of claim 1 wherein the plurality of two dimensional scans comprise scans with varying angles of incidence.

6. The method of claim 1 further comprising:
visualizing a three-dimensional volume representing the solid rotor.

7. The method of claim 1 wherein the kernel function is a triangle kernel function.

8. An apparatus comprising:
means for generating a three dimensional visualization of a solid rotor based on a plurality of two dimensional ultrasound scans of the solid rotor comprising:
means for associating each of a plurality of sample points of the plurality of two dimensional ultrasound scans with a corresponding 3D image point of a blank regular 3D grid;
means for determining a kernel function for each of the plurality of sample points defining a size and shape of a kernel located at the corresponding image point;
means for assigning a weight to each kernel; and
means for determining a value for each image point of a plurality of image points on the regular 3D grid based on kernels overlapping that image point.

9. The apparatus of claim 8 further comprising:
means for receiving the plurality of two dimensional ultrasound scans.

10. The apparatus of claim 9 wherein the plurality of two dimensional scans are acquired using a phased array transducer.

11. The apparatus of claim 8 wherein the kernel associated with the sample point is one of isotropic and elliptical form.

12. The apparatus of claim 8 wherein the plurality of two dimensional scans comprise scans with varying angles of incidence.

13. The apparatus of claim 8 further comprising:
means for visualizing a three-dimensional volume representing the solid rotor.

14. The apparatus of claim 8 wherein the kernel function is a triangle kernel function.

15. A non-transitory computer readable medium encoded with computer executable instructions defining steps comprising:
generating a three dimensional visualization of a solid rotor based on a plurality of two dimensional ultrasound scans of the solid rotor by:
associating each of a plurality of sample points of the plurality of two dimensional ultrasound scans with a corresponding 3D image point of a blank regular 3D grid;
determining a kernel function for each of the plurality of sample points defining a size and shape of a kernel located at the corresponding image point;
assigning a weight to each kernel; and
for each of a plurality of image points on the regular 3D grid, determining a value for that image point based on kernels overlapping that image point.

16. The computer readable medium of claim 15 further comprising computer executable instructions defining the step of:
  receiving the plurality of two dimensional ultrasound scans.

17. The computer readable medium of claim 16 wherein the plurality of two dimensional scans are acquired using a phased array transducer.

18. The computer readable medium of claim 15 wherein the kernel associated with the sample point is one of isotropic and elliptical form.

19. The computer readable medium of claim 15 wherein the plurality of two dimensional scans comprise scans with varying angles of incidence.

20. The computer readable medium of claim 15 further comprising computer executable instructions defining the step of:
  visualizing a three-dimensional volume representing the solid rotor.

21. The computer readable medium of claim 15 wherein the kernel function is a triangle kernel function.

* * * * *